(12) United States Patent
da Cruz

(10) Patent No.: US 8,507,652 B2
(45) Date of Patent: Aug. 13, 2013

(54) PHARMACEUTICAL COMPOSITION, DRESSING AND METHOD FOR TREATING SKIN LESION, INTERMEDIATE COMPOSITION AND PROCESS FOR PREPARING SAID DRESSING, AND USE OF CERIUM SALT ASSOCIATED WITH A COLLAGEN MATRIX

(76) Inventor: Luis Eduardo da Cruz, Barra de Tijuca (BR)

( * ) Notice: Subject to any disclaimer, the term of this patent is extended or adjusted under 35 U.S.C. 154(b) by 0 days.

(21) Appl. No.: 12/866,726

(22) PCT Filed: Feb. 9, 2009

(86) PCT No.: PCT/BR2009/000031
§ 371 (c)(1),
(2), (4) Date: Nov. 8, 2010

(87) PCT Pub. No.: WO2009/097672
PCT Pub. Date: Aug. 13, 2009

(65) Prior Publication Data
US 2011/0045072 A1 Feb. 24, 2011

Related U.S. Application Data

(63) Continuation-in-part of application No. 12/202,599, filed on Sep. 2, 2008, now abandoned.

(30) Foreign Application Priority Data

Feb. 8, 2008 (BR) ..................................... 0800085

(51) Int. Cl.
*A61K 38/17* (2006.01)
(52) U.S. Cl.
USPC ....................................................... 530/356
(58) Field of Classification Search
None
See application file for complete search history.

(56) References Cited

U.S. PATENT DOCUMENTS

| | | | |
|---|---|---|---|
| 4,088,754 A * | 5/1978 | Monafo ........................ | 424/617 |
| 4,746,504 A | 5/1988 | Nimrod et al. | |
| 5,441,741 A | 8/1995 | Cheong et al. | |
| 2003/0008830 A1 * | 1/2003 | Prozillo ........................ | 514/21 |

FOREIGN PATENT DOCUMENTS

| | | |
|---|---|---|
| EP | 0407943 A1 | 1/1991 |
| FR | 2759692 | 8/1998 |
| WO | WO-9111206 | 8/1991 |

OTHER PUBLICATIONS

Definition of "composition" (http://dictionary.reference.com/browse/composition)—downloaded May 28, 2012.*
Garner et al. (2005). "Cerium nitrate in the management of burns," Burns 31(5):539-547.
International Search Report (mailed Apr. 1, 2010) and Written Opinion, for PCT Application No. PCT/BR2009/000031 filed Feb. 9, 2009. 12 pages.
Lewandowski et al. (2004). "The Effect Of Adding Cerium Nitrate To Preparations With A Silver Salt Of Sulfathiazole On Survival Of *Staphylococcus aureus* Cells In Planktonic Form And Resident On The Skin", Wiadomosci Lekarskie [Medical News] vol. 57, No. 7-8, pp. 327-300. Translation dated Mar. 10, 2010.
Fleming et al. (1959). "Studies of the Irritating Action of Methylcellulose", AMA Arch Ophthalmol. vol. 61, No. 4, pp. 565-567.
Sipos et al. "Special Wound Healing Methods Used in Ancient Egypt and the Mythological Background," World Journal of Surgery, vol. 28, No. 2, pp. 211-216, Feb. 2004.
Mandelbaum et al., "Cicatrization: current concepts and auxiliary resources—part I and part II," An bras Dermatol, vol. 78, No. 4 and 5, pp. 393-410, Jul./Aug. 2003 and pp. 525-542, Sep./Oct. 2003.
Odland, "The Fine Structure of the interrelationship of Cells in the Human Epidermis," J. Biophysic and Biochem Cytol. vol. 4, No. 5, pp. 529-556, Mar. 11, 1958.
Choucalr et al., "Chapter 270: Wound Dressings," In Freedberg, IM eds. Fitzpatrick's Dermatology in General Medicine, International Edition, 1999:2954-1 958.
Winter, "Formation of the Scab and the Rate of Epithelization of Superficial Wounds in the Skin of the Young Domestic Pig," Nature, vol. 193, pp. 293-294, Jan. 20, 1962.
Hinman et al., "Effect of Air Exposure and Occlusion on Experimental Human Skin Wounds," Nature, vol. 200, pp. 377-378, Oct. 26, 1963.
Fitzpatrick Clark RAF, "Chapter 27—Mechanisms of Cutaneous Wound Repair," In Freedberg, IM eds. Fitzpatrick's Dermatology in General Medicine, International Edition, 1999:2954-1 958.
Hughes, "The Science of Wound Healing," The Oxford European Wound Healing Course Book, pp. 11-19, 2002.
Karukonda et al., "The effects of drugs on wound healing: part I," Int. Journal of Dermatology, vol. 39; pp. 250-257, 2000.
Karukonda et al., "The effects of drugs on wound healing: part II. Specific classes of drugs and their effect on healing wounds," Int. Journal of Dermatology, vol. 39; pp. 321-333, 2000.
Hart et al., "The role of oxidized regenerated cellulose/collagen in wound repair: effects in vitro on fibroblast biology and in vivo in a model of compromised healing," The Intl. Journal of Biochemistry & Cell Biology, vol. 34, pp. 1557-1570, 2002.
Mendez et al., "The proliferative capacity of neonatal skin fibroblasts is reduced after exposure to venous ulcer wound fluid: A potential mechanism for senescence in venous ulcers," J. of Vasc Surgery, vol. 30, No. 4, pp. 734-743, Oct. 1999.

(Continued)

*Primary Examiner* — Suzanne M Noakes
(74) *Attorney, Agent, or Firm* — Morrison & Foerster LLP

(57) ABSTRACT

The present invention refers to a pharmaceutical composition for treating skin lesion, comprising a cerium salt on a collagen matrix and a dermatologically acceptable carrier. In addition, the present invention also provides an intermediate composition for preparing a dressing for treating skin lesion and a process for preparing such dressing by lyophilizing said intermediate composition. The present invention also refers to a dressing for treating skin lesion, comprising a cerium salt on a collagen matrix, as well as to the use of a cerium salt associated with collagen in the preparation of the pharmaceutical composition or dressing according to the present invention. Another embodiment of the present invention is a method for treating skin lesion by applying such pharmaceutical composition or dressing on said skin lesion. The composition or dressing of the present invention can be used in topical applications in a variety of lesion types, such as skin lesions involving the release of toxins related to microbial proteins on human or animal organisms, or those so-called HSPs (heat shock proteins); burns which involve burned skin toxin formation or LPC (lipoprotein complex); chronically ulcerate skin lesions in which there is an overproduction of proteinase; skin lesions of difficult resolution, in which control of exudate overproduction is required; and critically infected or colonized skin lesions.

40 Claims, No Drawings

(56) References Cited

OTHER PUBLICATIONS

Vu et al., "Matrix metalloproteinases: effectors of development and normal physiology," Genes and Development, vol. 14, pp. 2123-2133, 2000.

Steffensen et al., "Proteolytic Events of Wound-Healing—Coordinated Interactions Among Matrix Metalloproteinases (MMPs), Integrins, and Extracellular Matrix Molecules," Crit Rev Oral Biol Med, vol. 12, No. 5, pp. 373-398, 2001.

Armstrong et al., "The Role of Matrix Metalloproteinases in Wound Healing," Journal of American Podiatric Medical Association, vol. 92, No. 1, pp. 12-18, 2002.

Postlethwalte et al., "Chemotactic attraction of human fibroblasts to type I, II, and III collagens and collagen-derived peptides," Proc. Natl. Acad. Sci. USA, vol. 75, No. 2, pp. 871-875, Feb. 1978.

Damsky et al., "Signal transduction by integrin receptors for extracellular matrix: cooperative processing of extracellular information," Curr Opin Cell Biol., vol. 4, No. 5, pp. 772-781, Oct. 1992.

Xu et al., "Extracellular Matrix Alters PDGF Regulation of Fibroblast Integrins," Journal of Cell Biology, vol. 132, Nos. 1&2, pp. 239-249, Jan. 1996.

Lin et al., "Multi-faceted regulation of cell differentiation by extracellular matrix," The FASEB Journal, vol. 7, pp. 737-743, Jun. 1993.

Wayner et al., "Identification of Multiple Cell Adhesion Receptors for Collagen and Fibronectin in Human Fibrosarcoma Cells Possessing Unique .alpha. and Common .beta. Subunits," Journal of Cell Biology, vol. 105, pp. 1873-1884, Oct. 1987.

Staatz et al., "The Membrane Glycoprotein Ia-IIa (VLA-2) Complex Mediates the Mg++-dependent Adhesion of Platelets to Collagen," Journal of Cell Biology, vol. 108, pp. 1917-1924, May 1989.

Ignatius et al., "Molecular Cloning of the Rat Integrin .alpha.1-Subunit: A Receptor of Laminin and Collagen," Journal of cell Biology, vol. 111, pp. 709-720, Aug. 1990.

Levenson et al., "The Healing of Rat Skin Wounds," Annals of Surgery, vol. 161, pp. 293-308, Feb. 1965.

Monafo, "The use of topical cerium nitrate-silver sulfadiazine in major burn injuries," Pan. Med., vol. 25, pp. 151-154, 1983.

Burkes et al., "The Bacteriostatic Activity of Cerium, Lanthanum, and Thallium," J. Bacteriology, vol. 54, pp. 417-425, Jun. 1947.

Monafo et al., "Cerium nitrate: A new topical antiseptic for extensive burns," Surgery, vol. 80, No. 4, pp. 465-473, Oct. 1976.

Fox et al., "Topical Chemotherapy for Burns Using Cerium Salts and Silver Sulfadiazine," Surgery, Gynecology & Obstetrics, vol. 144, pp. 668-672, 1977.

Allgower et al., "Burning the largest immune organ," Burns, vol. 22, Suppl. 1, pp. 7-47, 1995.

Deveci et al., "Effects of cerium nitrate bathing and prompt burn wound excision on IL-6 and TNF-.alpha. levels in burned rats," Burns, vol. 26, pp. 41-45, 2000.

Office Action received for European Patent Application No. 09707825.7, mailed on Nov. 4, 2011, 6 pages.

International Preliminary Report on Patentability received for PCT Patent Application No. PCT/BR2009/000031, issued on Aug. 10, 2010, 8 pages.

\* cited by examiner

PHARMACEUTICAL COMPOSITION, DRESSING AND METHOD FOR TREATING SKIN LESION, INTERMEDIATE COMPOSITION AND PROCESS FOR PREPARING SAID DRESSING, AND USE OF CERIUM SALT ASSOCIATED WITH A COLLAGEN MATRIX

CROSS REFERENCE TO RELATED APPLICATIONS

This is a U.S. National Phase patent application of PCT/BR2009/000031, filed Feb. 9, 2009, which claims priority to U.S. patent application Ser. No. 12/202,599, filed Sep. 2, 2008, which claims priority to Brazil Provisional patent application Serial No. PI0800085-8, filed Feb. 2, 2008, all of which are hereby incorporated by reference in the present disclosure in their entirety.

FIELD OF THE INVENTION

The present invention refers to a pharmaceutical composition for treating skin lesion, comprising a cerium salt on a collagen matrix and a dermatologically acceptable carrier.

In addition, the present invention also provides an intermediate composition for preparing a dressing for treating skin lesion and a process for preparing such dressing by lyophilizing said intermediate composition.

The present invention also refers to a dressing for treating skin lesion, comprising a cerium salt on a collagen matrix, as well as to the use of a cerium salt associated with collagen in the preparation of the pharmaceutical composition or dressing according to the present invention.

Another embodiment of the present invention is a method for treating skin lesion by applying such pharmaceutical composition or dressing on said skin lesion.

The composition or dressing of the present invention can be used in topical applications in a variety of lesion types, such as skin lesions involving the release of toxins related to microbial proteins on human or animal organisms, or those so-called HSPs (heat shock proteins); burns which involve burned skin toxin formation or LPC (lipoprotein complex); chronically ulcerate skin lesions in which there is an overproduction of proteinase; skin lesions of difficult resolution, in which control of exudate overproduction is required; and critically infected or colonized skin lesions.

Historical Aspects

In contemporary medical practice, wound healing treatment is based on the use of dressings, base illnesses control, debridement of non-viable tissue, homeostasis, restoration of adequate tissue perfusion, pressure limitation over wounded spot and infection control[1].

From a historical point of view, many things have changed on wound treatment approach until present concepts are reached. In ancient Egypt, a wound was seen as a hole through which evil beings coming from hell could enter a person's body. Interpreting things like this, excrement would be applied over the lesion hoping this could send even the worst of demons away[1]. One of the most popular drugs used in ancient Egypt was honey. Nowadays, its therapeutic properties are attributed to repressing microorganism growth and, for the fact of being hygroscopic, to attracting leukocyte and antibodies to the wounded spot.

As far as wound dressings are concerned, the Egyptian used to apply a technology similar to that used in the mummies embalming process. Bandages were used to cover and keep medicine in the desired body spots[1]. Lynen produced in Egypt would vary in texture from fine gauze-like fibers used nowadays to thicker fabric as the ones used with mummies. For lesion debridement there are descriptions of treatment with larvae, able to develop proteolytic enzymes which degenerate the necrotic tissue and liquefy it[1].

Hypocrites used to recommend cleaning the wounds with warm water, wine and vinegar[2] and drying it. The concept that the wound should be kept dry to provide better healing conditions persisted until the end of the II World War[2]. From then radical changes regarding the basic concepts of wound healing took place. In 1958, Odland saw that the bottom part of a blister would heal faster if its surface was not removed[3,4]. Later, using lesions of a domesticated pig as a model, Winter showed a faster epithelium repair after occlusion, thus revolutionizing the approach towards wound care[5]. Then came 1963 and Hinman et al. established the beneficial effect of wound occlusion in human beings[6].

Presently, the wide range of wound healers aiming at not only keeping the spot humid as well as other actions, such as antimicrobial properties, are available in the market.

Theoretical Basis

Basic Wound Repair Concepts

Far beyond the linear concept triggered by growth factor processes over inflammatory cells, repair represents interaction among soluble mediators, extracellular matrix and parenchyma cells[7]. The extracellular matrix molecules can provide signals to genetic expression through integrin receptors and tissue cells interaction with the matrix can change the phenotypes as well as cell functions[7,8].

Tissue trauma is followed by a series of events which can be studied divided in phases (homeostasis, inflammatory, tissue formation and wound remodeling). However, these are not mutually exclusive allowing for temporal superposition.

Tissue aggression and the consequent burst of blood vessels will trigger a first sequence of events that will culminate in coagulation, or clotting. The blood clot formed is useful to keep homeostasis, besides providing the provisory matrix for cell migration.

Platelets adhere to interstitial connective tissue and later aggregate to each other. In this aggregation process they release several mediators and express clotting factors. Fibrin clot and thrombin formed on the spot act as a nest for adhesion and aggregation of additional platelets. Platelets fibrinogen, once converted into fibrin by the thrombin, contributes to the fibrin clot.

Platelets have to be considered at this moment, not only for their important role in the making of the homeostatic cover as well as by releasing the cytokines and growth factors exemplified in the Platelets Derived Growth Factor (PDGF) and the Transforming Growth Factor □ and □ (TGF□ and TGF □).

Besides that, the clotting cascade itself, complement compounds and damaged cells, generate a number of chemotactic factors which when in association attract leukocytes to the damaged spot. Endothelial activation by chemotactic stimulates also the endothelial release of elastase and collagenase molecules which, in turn, ease cellular penetration through blood vessels basal membranes.

Leukocyte will perform the cleaning of foreign bodies and bacteria found in the system. Their persistence in the place can extend the inflammatory stage and difficult normal repair. On the other hand, generating chemotactic agents of the wound is generally reduced as it is kept "clean". The neutrophil residue will gradually be expelled with the scab or phagocytized by macrophages or fibroblasts.

Responding to specific chemotactic factors, such as elastin, fibronectin, collagen fragments and TGF □, peripheral blood monocyte continue to be recruited by the wound where they are activated and show a macrophage phenotype. These cells, as well as the platelets start granulation tissue formation. Macrophages are able to debride the tissue, digesting pathogenic organisms, tissue debris and worn out neutrophils. Macrophage seem to perform a fundamental role in the transition between inflammation and repair since they secret fibroblasts growing factors needed to start and spread the tissue remodeling in wounds.

Some hours after the aggression, keratinocytes of the epithelium residual frames move across the wound. Important phenotype changes are observed in the epithelium cells as retraction of the intercellular tonofilaments, dissolution of the intercellular desmosome in their majority, forming of peripheral cytoplasm actin filaments and loss of firm links between dermis and epidermis, which allows epidermis cells to display lateral motility.

Until two days after aggression, the epithelium cells on the edge of the wound start to migrate. Keratinocytes migrating over the wound do not run randomly over a provisory matrix area but really "spare" viable tissue from non-viable tissue. This migration route is mediated by the integrins expressed by the epidermis cells in their membranes, as for example, the keratinocytes do not express receptors to fibrinogen, fibrin, denatured collagen or fibronectin. Thus, migratory epidermis cells avoid clot rich in fibrin/fibronectin and migrate over collagen type I. In the end, keratinocytes migration brings scab discard.

Simultaneously to the re-epithelialization, proteins from the basal membrane appear again from the edges of the wound to the center. Epidermis cells return to their normal phenotype, firmly sticking to the basal membrane through hemidesmosome and to the neodermis through collagen type VII fibrils.

After approximately four days of aggression, granulating tissue starts to form. It got its name from the granulated appearance seen when it is incised, due to the presence of many newly-formed capillaries.

Angiogenesis is, in a few words, a process mediated by four related phenomena: change in cellular phenotype, induced migration by chemostatic, mitogen stimulation and the appropriate extracellular matrix.

Besides vascular proliferation, fibroplasia is a marked element in the granulation tissue. Platelets and macrophage release a series of cytokine with proliferative and migratory activities to fibroblasts. Later, the fibroblasts themselves will produce cytokine and respond to them in an autocrine way.

For the fibroblasts to migrate an active proteolysis system able to cleave a way for the migration is necessary. Various enzymes derived from fibroblasts, together with the plasmin coming from the serum, seem to perform this role. Those include plasminogen activator, interstitial colagenase (matrix metalloproteinase 1, MMP-1), gelatinase (MMP-2) and estromelisin (MMP-3), as well as serum-derived plasminogen.

Matrix Metalloproteinases (MMP) are a family of extracellular proteinases responsible for regulating physiological events, not only the remodeling of the extracellular matrix but also influencing other cellular activities, as proliferation and apoptosis. Their action is fine tuned through tissue inhibitors of metalloproteinases (TIMP) and growth factors. Chemotactic factor PDGF, for instance, stimulates the release of these enzymes by the fibroblasts while TGF induces secretion of proteinase inhibitors, in a display of detailed control of extracellular matrix degradation during fibroblasts migration.

Fibroblasts, as macrophages and newly-formed blood vessels, cleave the fibrin clot as they migrate to the wounded spot and lay a new provisory matrix made of hyaluronan and fibronectin. The extracellular matrix, in turn, affects the fibroblasts in their functions of synthesis and re-shape of the matrix itself, interaction known as dynamic reciprocity.

The following stage is marked by the production of a collagen matrix. Summarizing, during skin repair, connective tissue matrix dismissal happens in a sequence set of fibronectin, collagen type III and, later, collagen type I. Production of the latter coincides with an enhancement of wound resistance. Collagen type V will also be enhanced during the granulation tissue development in parallel to the vascularization of the tissue. Besides providing structural support for new tissue resistance, collagen acts on matrix-immersed cells, for example, changing their cellular phenotype or working as a chemotactic element.

After the collagen matrix dismissal, the fibroblasts reshape it and provoke wound contraction. These cells take the phenotype of smooth muscle cells known as myofibroblasts which, through a link to the extracellular matrix (fibronectin and collagen) and to each other, lead to connective tissue compression and wound contraction. Transmission of traction forces depend basically on fibroblasts connection to collagen matrix via the integrin receptors and crossed links among individual collagen bundles.

Transition from a granulation tissue rich in fibroblasts to a relatively acellular matrix are followed from the cellular point of view by fibroblast apoptosis around the tenth day of repair. Capillae regression happens from one to two days after removal of the angiogenesis stimuli, made through another apoptosis via.

Wound remodeling stage is marked by the extracellular matrix remodeling and cellular differentiation or apoptosis. The composition and extracellular matrix granulation tissue structure is a function of time interval and distance between the edges of the wound, that is, on larger wounds, extracellular matrix remodeling and maturation of neo-epidermis, fibroplasia and neovascularization start from the edge of the wound while granulation tissue formation continues to move towards the most central part of the lesion. This makes the extracellular matrix of the wound edges differ from the central extracellular matrix regarding both the qualitative and the quantitative approaches.

The first cell types to undergo apoptosis are the endothelium cells, with a reduction in the capillae number. It will later happen to myofibroblasts and macrophages leading to more acellular wound repair. The extracellular matrix goes on modifying itself along the following months and years, though slowly.

Some Influencing Factors on Skin Wound Repair

Many factors, both local and systemic, may influence the tissue wound healing process creating unfavorable outcomes, as hypertrophic scars or keloids or even chronic ulcers, as leg ulcers, pressure ulcers and perforating plantar wounds.

It is well know, for example, that due to the richness of the skin annexes, facial lesions will be repaired faster than lesions on the feet. Low temperatures or blood flow deficiencies can also compromise the wound repair process.

Additionally, other local factors as anoxia, abnormal pH, necrosis, infection, hematoma and foreign bodies can compromise tissue repair. Hypoxia favors tissue migration and angiogenesis while compromising cell proliferation, collagen synthesis and resistance against bacteria.

On wounds where the repair evolves naturally there is a balance between the MMPs and TIMPs expressions; on the other hand, on chronic ulcerate lesions, as leg ulcers, there is growing evidence of a local proteolysis increase. Hart et al.[13] highlight that the destructive action of these high levels of proteases can be a compromising factor to wound healing in chronic ulcers. The excessive activity of proteinase seem to deprive wounds of having an initial matrix that could work as a lead to cell migration and framework for matrix storage and growth factor keeping, key elements involved in orchestrating the new tissue making process. A high proteases activity level can even cause damage to cellular surface proteins as growth factors receptors and integrins receptors, damage enough to create an impact on the activity of all cells engaged on the tissue repair process.

Infection is an important cause of repair delay. Although almost all skin wounds are contaminated by the existing flora, pathogenic organisms need to represent a value over the 100.000 bacteria per gram of tissue mark if the clinic infection is to happen. If bacterial colonization is evaluated as critical, it can provoke a longer than desired inflammatory stage and thus compromise repair and if so, should be treated with topical antiseptics.

In optimized wound repair timelines, one should also drain any hematoma and avoid drugs that ease their formation, as anti-clotting and anti-platelet agents. Foreign bodies represent a fitting place for bacteria adherence, reducing oxygen tension and wound pH, so they must be removed.

Regarding systemic factors, both the nutritional features and the quality of life (smoking, alcohol abuse), the use of some drugs (as corticosteroids) or systemic diseases, as diabetes mellitus, can compromise the progress of wound repair process. Old-age patients show a reduction in their protein synthesis, delayed lymphocitary migration and a persisting inflammatory stage, besides being subject to malnutrition risks, concomitant diseases and use of medicament.

The fluid seen in chronic ulcers, as pressure ulcers, venous stasis ulcers and diabetic foot, all inhibit cellular proliferation, mainly of fibroblasts. This fluid is rich in tumor necrosis factor (TNF α). It is supposed that substances able to reduce the level of this cytokine, such as cerium nitrate, can positively module chronic ulcers repair.

Lastly, apart from what was thought in the past, there is presently clear evidence that a dried wound will not heal as well as one treated on a humid environment. The benefits of a humid environment include the promotion of re-ephitalialization, dermis repair and angiogenesis. Topical medicine and occlusive dressings provide a humid environment that helps in the wound repair.

Collagen

Collagens are glycoprotein of extracellular matrix composed of three chains and forming triple helix along part of their primary sequence. There are 18 types of appointed collagen, from I to XVIII according to the date they were discovered.

The majority of the studies made over the content of collagen found in repairing wounds and artificially induced granulation tissue (implanted sponges) has examined collagen types I and III, since these two types of collagen have been characterized for some time and their supramolecular structures are clearly established.

Hard helical collagen macromolecules aggregated in fibril sheaves gradually give repair tissue an enhancement in tensile strength and firmness. Besides working to support structure for the new tissue resistance, collagen can have a profound effect on matrix-immersed cells. Peptides derived from collagen, for instance, work as chemotactic for in vitro fibroblasts[18] and can have a similar in vivo effect. Furthermore, intact collagen can change the phenotype and function of a variety of different cells[19-21]. These effects can be partially measured through the activation of integrin receptors for collagen $\alpha_1\beta_1$ and $\alpha_2\beta_1$[22-24].

Collagen re-shape during the transition period of granulation tissue for a mature repair is dependent on both the continuous synthesis of the collagen as well as on the collagen catabolism. Collagen degradation on wound is controlled by a variety of collagenase enzymes of granulocytes, macrophages, epidermis cells and fibroblasts. These activities are controlled by various similar inhibitors known as tissue inhibitors of metalloproteinases (TIMP), which are then regulated during development and seemingly during wound repair. Cytokines as the TGF β, PDGF and IL-1 and the extracellular matrix itself can perform an important role in modulating collagenase and TIMP in vivo expression.

Wounds gain only about 20 percent of their final strength on the third week, during which fibrillar collagen accumulated relatively fast and was systematically re-shaped by wound contraction driven by the myofibroblasts. In fact, gradual gain in tension power is less related to new collagen dismissal than to additional collagen re-shape, thicker formation of collagen sheaves and a change to cross molecule links. So, the wounded tissue does not have the same resistance than the non-wounded skin. In its maximum resistance output, a scar will have the maximum of 70 percent of the power of the intact skin[25].

Hart et al.[13] showed that dressings made from collagen are capable of absorbing a wide range of factors present in chronic ulcers and able of making the healing process more difficult, as proteases, free radicals, and ferric ions. Besides that, they have also reported dressings made from collagen are able to attach to one another and protect growth factors like PDGF, maintaining their biological activity and making the environment even more favorable to skin repair.

In ulcers, applied collagen will work as hemostatic, chemotactic and as a matrix for cell migration. Further, it can get linked and inactivate matrix metalloproteinase present in excess in chronic ulcers, and in these conditions, harmful to the tissue repair process. On the other hand, growth factors will be kept in contact with the wound bed and protected from action of proteases. The fact it is bio-compatible is yet another positive point favoring the use of the collagen matrix.

Cerium Salt

The metal cerium holds powerful anti-microbial action and presents low toxicity towards mammal cells[26]. Burkes & McCleskey[27] have shown that cerium salts are toxic in vitro to bacteria and fungi. In 39 bacteria species studied, cerium nitrate inhibited the growth in concentrations in the order of 0.0004M[27]. Although the biochemical levels in which cerium exerts its bacteriostatic effects are still unknown, the possibilities are many. A change in bacteria cell walls negative charge has been reported, leading to the migration and agglutination of microorganisms[28]. Lanthanide also responds to nucleic acid and makes insoluble complexes[28].

It has been shown that human burns when in contact with cerium salts for weeks were less frequently colonized by Gram negative bacteria[26]. Fox et al. (1977)[29] reported the association of cerium nitrate and silver sulfadiazine resulting in an increase in clinic efficacy for patients with severe burns. Observations have confirmed topical cerium reverted T lymphocyte failure common to burns. This beneficial effect is related to cerium link to a lipoprotein complex (LPC) existent on burn lesion[30].

Tumor necrosis factor (TNF-α) is the most powerful inflammatory cytokine. It is well known that excessive release of cytokines has a harmful action over the immunological function. Deveci et al.[31] demonstrated that treating lesions to cerium nitrate (CN) resulted in an increase of interleucin-6 and in a reduction of TNF-α, limiting the extent of the inflammatory reaction. There are then evidences that this metal is useful in treating chronic lesions, by the unorganized presence of mediators of the inflammatory response, like interleukins and TNF[14, 31].

Within the context of chronic ulcers and burns, the advantages of adding cerium nitrate to a dressing are: antimicrobial action, immuno modulating action, anti-inflammatory action by reducing levels of TNF-☐.

SUMMARY OF THE INVENTION

The present invention refers to obtaining a cell proliferation matrix, particularly in the form of a non-lyophilized or lyophilized (dressing) composition, as well as its clinical applications, which generally correspond to the treatment given to lesions in characterized by loss of cutaneous integrity, including skin mucous ulcers of different etiologies, acting as hemostatic, topical healing, antimicrobial agent and/or immunomodulator agent.

The highlight of the composition or dressing of the present invention is the association of cerium, a metal from the lanthanide series, to a collagen matrix.

DESCRIPTION OF THE INVENTION

The invention refers to the production of a cellular proliferation matrix, particularly in the form of a non-lyophilized or lyophilized (dressing) composition, comprising bovine collagen in association with a cerium salt and, optionally, an alginate, with hemostatic, wound repairing, antimicrobial, immunomodulating properties, able to absorb exudates excess, keeping the environment humid and, at the same time, preventing maceration of the lesion. Its therapeutic action is related to treating the infection and wound colonization, as a result of its wide spectrum of antimicrobial action.

The wound healing properties of the composition or dressing of the present invention come from collagen acting as a structural support and facilitating cell migration besides performing a protective role for the newly-produced collagen in a collagenase-rich environment, common in chronic ulcers. Additionally, the presence of toxins on the burn-affected skin, like LPC (lipoprotein complex), and that of inflammatory cytokines largely produced in the environment of chronic ulcers, as Tumor Necrosis Factor-Alfa, can perpetuate the inflammatory reaction, that can be modulated by the presence of the metal cerium. Conjugating together wound repairing, anti-microbial and immunomodulator actions, will make the dressing of the present invention an efficient therapeutic agent for burns and wounds of different etiologies, such as venous stasis ulcers, pressure ulcers, plantar skin ulcers, complicated surgical wounds and burns.

The composition of the present invention, in its non-lyophilized form, has the appearance of an opaque gel and may be lyophilized as a dressing of varying sizes. The process used for preparing such dressing according to the present invention comprises dissolving the cerium salt, particularly cerium nitrate, in a dermatologically acceptable carrier, preferably water, adding the solution of cerium salt to collagen and homogenizing it. In a preferred embodiment, the mixture obtained may be homogenized to an alginate dispersion into an emollient, preferably propylene glycol, until it becomes a uniform mass. Then the resulting mass is molded in specific patterns according to desired formats and subsequently freeze dried (lyophilized). After freeze drying (lyophilization) carried out by conventional techniques known in the art, the product presents a spongy aspect, similar to a fiber frame. The end product may then be sterilized through gamma radiation, ethylene oxide or electron beam sterilization systems.

DETAILED DESCRIPTION OF THE INVENTION

The present invention refers to a pharmaceutical composition for treating skin lesion comprising a cerium salt over a collagen matrix and a dermatologically acceptable carrier.

Preferably, the cerium salt used is the cerium nitrate, in particular hexahydrated cerium nitrate, and the collagen used is bovine collagen type I.

Cerium salt may be present in the pharmaceutical composition in an amount ranging from 0.1% to 5% by weight and the collagen may be in the gel form varying from 1% to 95% by weight, based on the total weight of the composition. Preferably, cerium salt is present in an amount from 0.4% to 2.2% by weight and the collagen gel is present in an amount from 73% to 75% by weight, based on the total weight of the composition.

In a preferred embodiment of the invention, cerium salt is present in an amount of 0.4% by weight and the collagen gel is present in an amount of 75% by weight, based on the total weight of the composition.

In another preferred embodiment, cerium salt is present in an amount of 2.2% by weight and collagen gel is present in an amount of 73% by weight, based on the total weight of the composition.

The pharmaceutical composition of the present invention may also include a suspending agent. Preferably, this suspending agent is an alginate, which may be chosen from sodium alginate and calcium alginate. The suspension agent may be present in an amount ranging from 0.1% to 20% by weight, based on the total weight of the composition, preferably from 0.1% a 15% by weight, particularly 10% by weight.

The dermatologically acceptable carrier used in the composition of the present invention is preferably water.

The pharmaceutical composition of the present invention may also comprise an emollient, preferably propylene glycol, which may be present in an amount from 1% to 20% by weight, based on the total weight of the composition, preferably from 5% to 15% by weight, particularly 10% by weight.

The pharmaceutical composition of the present invention may be used in topical applications in a variety of lesion types, such as skin lesions involving the release of toxins related to microbial proteins on human or animal organisms, or those so-called HSP (heat shock proteins); burns which involve burned skin toxin formation or LPC; chronically ulcerate skin lesions in which there is an overproduction of proteinase; skin lesions of difficult resolution, in which control of exudate overproduction is required; and critically infected or colonized skin lesions.

The present invention also refers to an intermediate composition for preparing a dressing for treating skin lesion, such composition comprising a cerium salt over a collagen matrix and a dermatologically acceptable carrier.

Preferably, the cerium salt used is the cerium nitrate, in particular hexahydrated cerium nitrate, and the collagen used is bovine collagen type I.

Cerium salt may be present in the intermediate composition in an amount ranging from 0.001% to 5% by weight and the collagen may be in the gel form varying from 1% to 95% by weight, based on the total weight of the composition.

In a preferred embodiment of the invention, cerium salt is present in an amount of 0.014% by weight and the collagen gel is present in an amount of 75% by weight, based on the total weight of the composition.

In another preferred embodiment, cerium salt is present in an amount of 0.075% by weight and collagen gel is present in an amount of 73% by weight, based on the total weight of the composition.

The intermediate composition of the present invention may also include a suspending agent. Preferably, this suspending agent is an alginate, which may be chosen from sodium alginate and calcium alginate. The suspension agent may be present in an amount ranging from 0.1% to 20% by weight, based on the total weight of the composition, preferably from 0.1% a 15% by weight, particularly 0.35% by weight.

The dermatologically acceptable carrier used in the intermediate composition of the present invention is preferably water.

The intermediate composition of the present invention may also comprise an emollient, preferably propylene glycol, which may be present in an amount from 1% to 20% by weight, based on the total weight of the composition, preferably from 5% to 15% by weight, particularly 10% by weight.

The present invention is also related to a dressing for treating skin lesion comprising a cerium salt on a collagen matrix. Preferably, the cerium salt used is the cerium nitrate, in particular hexahydrated cerium nitrate, and the collagen used is bovine collagen type I.

Cerium salt may be present in the dressing in an amount ranging from 0.1% to 5% by weight, preferably from 0.4% to 2.2% by weight, based on the total weight of the dressing. Preferably, cerium salt is present in an amount of 0.4% by weight or in an amount of 2.2% by weight.

Preferably, the dressing is prepared by lyophilizing the intermediate composition of the present invention. Particularly, the dressing may be sterilized by gamma rays, ethylene oxide or electron beam.

Another embodiment of the present invention is related to a process for preparing a dressing for treating skin lesion, comprising the steps a) providing an intermediate composition as described herein above; and b) lyophilizing the intermediate composition of step a), thus forming the dressing for treating skin lesion.

The process further comprises the step of sterilizing the dressing formed in step b) through gamma radiation, ethylene oxide or electron beam sterilization systems.

The present invention also refers to the use of a cerium salt associated with a collagen in the preparation of a pharmaceutical composition, an intermediate composition or a dressing according to the present invention.

In addition, the present invention also refers to a method for treating skin lesion by applying a pharmaceutical composition or a dressing as disclosed herein on said skin lesion.

The present invention is characterized by the association of a repair-promoting substance (collagen) with an anti-microbial and immunomodulator substance (cerium salt, particularly cerium nitrate), in the form of a non-lyophilized or lyophilized (dressing) pharmaceutical composition. Another characteristic of the present invention is the development of a dressing formulation which works as a cell proliferation matrix with hemostatic, anti-microbial and immunomodulating properties, comprising collagen in association with a cerium salt, particularly cerium nitrate and optionally an (sodium or calcium) alginate.

ADVANTAGES OF THE INVENTION IN RELATION TO THE STATE OF THE ART

The pharmaceutical composition and the dressing of the present invention promote tissue repair through the biological effects of collagen, which works as a structural support and facilitates cell migration besides having a protective role of the newly-produced collagen in a collagenase-rich environment, common to chronic ulcers, in association with cerium salt antimicrobial and immunomodulating effects, described by severely burned patients and those suffering with chronic ulcers.

Preferably, a suspending agent may be used in the present invention. More preferably, the suspending agent is an alginate. Particularly, sodium or calcium alginate are used. The presence of the (sodium or calcium) alginate works as a lesion humidity control mechanism, absorbing exudate excess, thus avoiding wound edge maceration and keeping the ideal humidity level in the wound.

The pharmaceutical composition and the dressing of the present invention do not adhere to the wound bed, thus avoiding trauma during changes in the newly-formed tissue, and may be trimmed to the shape of the wound. In its range of applications, there are indications for wounds of difficult healing, even those with critical bacteria colonization levels or those over which infection develops, through the work of the cerium metal antimicrobial action. Its clinical applications are, therefore: burns, leg ulcers (venous stasis ulcers) artery and mixed ulcers, diabetic foot, pressure ulcers, surgical and trauma wounds.

In comparison with hydrocolloid dressings, the pharmaceutical composition and the dressing of the present invention have the advantages of acting over protein and microbial toxins or HSP proteins and present antimicrobial, hemostatic properties, besides modulating lesions with proteases excess.

There are other collagen-containing dressings in the market, such as Fibracol®, Fibracol Plus®, Promogran® (all three marketed by Johnson & Johnson), among others. Such dressings have the limitation of not having an antimicrobial action, which can be critical in some clinical instances, as it is the case of chronic ulcers. These kinds of ulcers are generally colonized by bacteria and it is known that critical levels of colonization are harmful to wound healing processes, even when devoid of infection. Products using only collagen, therefore, would have their application range widely limited to specific wound repair stages when no signal of infection or critical bacteria colonization could be detected and they should be replaced whenever these situations happen.

The pharmaceutical composition and the dressing of the present invention provide cerium salt, particularly cerium nitrate, and its antimicrobial activity, as an association to collagen. The same substance is present in another antimicrobial and wound-repairing cream available in the market, Dermacerium®, commercialized by Silvestre Labs (Brazil). Cerium salt, particularly cerium nitrate, brings additional property of immunomodulation, as already mentioned.

The cerium salt, particularly cerium nitrate, as an antimicrobial element present in the dressing was chosen due not only to its immunomodulating properties, but to the fact that there have been no relevant reports to date of the development of microbial resistance, even after years of use. The composition of the present invention formulated as dressings is more appropriate that in the form of cream since it does not need to be replaced frequently, thus reducing costs and specialized staff.

The market for dressings for different lesions is described in Table 1 below:

TABLE 1

| Type of Lesion | World Incidences (in million) | Healing Time (days) | Compound annual growth rate (CAGR) |
|---|---|---|---|
| Surgical Lesions | 97 | 14 | 3.1% |
| Trauma Lesions | 1.6 | 28 | 1.4% |
| Lacerations | 19.4 | 14 | 1.0% |
| Burns | 9.7 | 21 | 1.0% |
| Chronic Lesions | 26.3 | — | 7.4% |
| Carcinomas | 0.6 | 14 | 3.0% |
| Melanomas | 0.2 | 14 | 3.0% |
| Complex Skin Cancers | 0.2 | 28 | 3.0% |

Source: MedMarket Diligence, LLC

BEST MODE FOR CARRYING OUT THE INVENTION

Detailed illustrative embodiments of the invention disclosed herein exemplify the invention and are currently considered to be the best embodiments for such purposes. They are provided by way of illustration and not limitation of the invention. Various modifications thereof will occur to those skilled in the art, and such modifications are within the scope of the claims which define the present invention.

The best modes for carrying out the present invention are:

a) A pharmaceutical composition for treating skin lesion comprising 0.4% by weight of a cerium nitrate over a matrix comprising 75% by weight of bovine collagen type I gel and water, said composition comprising 10% by weight of propylene glycol as emollient and, optionally, 10% by weight of calcium or sodium alginate as a suspending agent;

b) A pharmaceutical composition for treating skin lesion comprising 2.2% by weight of a cerium nitrate over a matrix comprising 73% by weight of bovine collagen type I gel and water, said composition comprising 10% by weight of propylene glycol as emollient and, optionally, 10% by weight of calcium or sodium alginate as a suspending agent.

c) An intermediate composition for preparing a dressing for treating skin lesion comprising 0.014% by weight of a cerium nitrate over a matrix comprising 75% by weight of bovine collagen type I gel and water, said composition comprising 10% by weight of propylene glycol as emollient and, optionally, 0.35% by weight of calcium or sodium alginate as a suspending agent;

d) An intermediate composition for preparing a dressing for treating skin lesion comprising 0.075% by weight of a cerium nitrate over a matrix comprising from 73% by weight of bovine collagen type I gel and water, said composition comprising 10% by weight of propylene glycol as emollient and, optionally, 0.35% by weight of calcium or sodium alginate as a suspending agent.

e) A dressing for treating skin lesion comprising 0.4% or 2.2% by weight of a cerium nitrate, obtained from lyophilization of the intermediate compositions of items c) and d) above;

f) A process for preparing a dressing for treating skin lesion, comprising the steps of providing an intermediate composition of item c) or d); lyophilizing it to form the dressing; and sterilizing it through gamma radiation, ethylene oxide or electron beam sterilization systems.

g) A method for treating skin lesion by applying the pharmaceutical composition of items a) and b) above or the dressing of item e) above on the skin lesion.

Examples

Formulations 1 to 12 below were prepared according to the present invention. The process used for preparing such formulations comprises dissolving the cerium salt, particularly cerium nitrate, in a dermatologically acceptable carrier, preferably water, adding the solution of cerium salt to collagen gel and homogenizing the resulting mixture. For preparing Formulations 3-6 and 9-12, the mixture obtained was homogenized to an alginate dispersion into propylene glycol, until it became a uniform mass.

Formulations 1-6 are examples of the pharmaceutical compositions for treating skin lesion according to the present invention, comprising a cerium salt on a collagen matrix and a dermatologically acceptable carrier. They were prepared to be used as an end product containing cerium nitrate in a concentration of 0.4% by weight (Formulations 1, 3 and 4) and 2.2% by weight (Formulations 2, 5 and 6), bovine collagen type I in the gel form and water as the dermatologically acceptable carrier. Propylene glycol was used as emollient. Sodium alginate (Formulations 3 and 5) and calcium alginate (Formulations 4 and 6) were used as suspending agent and exudate absorber.

Formulation 1:

| Raw material | Preferred Concentration (% w/w) | Special Concentration (% w/w) | Properties |
|---|---|---|---|
| Bovine Collagen Type I (gel) | 1% to 95% | 75% | Hemostatic, chemotactic and matrix for cell migration |
| Cerium Nitrate | 0.1% to 5% | 0.4% | Antimicrobial agent, immunomodulator, anti-inflammatory (reduction of TNF-$\zeta$ levels). |
| Propylene Glycol | 1% to 20% | 10% | Emollient |
| Water | q.s.p. 100% | | Carrier |

Formulation 2:

| Raw material | Preferred Concentration (% w/w) | Special Concentration (% w/w) | Properties |
|---|---|---|---|
| Bovine Collagen Type I (gel) | 1% to 95% | 73% | Hemostatic, chemotactic and matrix for cell migration |
| Cerium Nitrate | 0.1% to 5% | 2.2% | Antimicrobial agent, immunomodulator, anti-inflammatory (reduction of TNF-$\zeta$ levels). |
| Propylene Glycol | 1% to 20% | 10% | Emollient |
| Water | q.s.p. 100% | | Carrier |

Formulation 3:

| Raw material | Preferred Concentration (% w/w) | Special Concentration (% w/w) | Properties |
|---|---|---|---|
| Bovine Collagen Type I (gel) | 1% to 95% | 75% | Hemostatic, chemotactic and matrix for cell migration |
| Cerium Nitrate | 0.1% to 5% | 0.4% | Antimicrobial agent, immunomodulator, anti-inflammatory (reduction of TNF-☐ levels). |
| Sodium alginate | 0.1% to 20% | 10% | Suspending agent, exudate absorber |
| Propylene Glycol | 1% to 20% | 10% | Emollient |
| Water | q.s.p. 100% | | Carrier |

Formulation 4:

| Raw material | Preferred Concentration (% w/w) | Special Concentration (% w/w) | Properties |
|---|---|---|---|
| Bovine Collagen Type I (gel) | 1% to 95% | 75% | Hemostatic, chemotactic and matrix for cell migration |
| Cerium Nitrate | 0.1% to 5% | 0.4% | Antimicrobial agent, immunomodulator, anti-inflammatory (reduction of TNF-☐ levels). |
| Calcium alginate | 0.1% to 20% | 10% | Suspending agent, exudate absorber |
| Propylene Glycol | 1% to 20% | 10% | Emollient |
| Water | q.s.p. 100% | | Carrier |

Formulation 5:

| Raw material | Preferred Concentration (% w/w) | Special concentration (% w/w) | Properties |
|---|---|---|---|
| Bovine collagen type I (gel) | 1% to 95% | 73% | Hemostatic, chemotactic and matrix for cell migration |
| Cerium Nitrate | 0.1% to 5% | 2.2% | Antimicrobial agent, immunomodulator, anti-inflammatory (reduction of TNF-☐ levels). |
| Sodium alginate | 0.1% to 20% | 10% | Suspending agent, exudate absorber |
| Propylene Glycol | 1% to 20% | 10% | Emollient |
| Water | q.s.p. 100% | | Carrier |

Formulation 6:

| Raw material | Preferred Concentration (% w/w) | Special concentration (% w/w) | Properties |
|---|---|---|---|
| Bovine collagen type I (gel) | 1% to 95% | 73% | Hemostatic, chemotactic and matrix for cell migration |
| Cerium Nitrate | 0.1% to 5% | 2.2% | Antimicrobial agent, immunomodulator, anti-inflammatory (reduction of TNF-☐ levels). |
| Calcium alginate | 0.1% to 20% | 10% | Suspending agent, exudate absorber |
| Propylene Glycol | 1% to 20% | 10% | Emollient |
| Water | q.s.p. 100% | | Carrier |

Formulations 7-12 below are examples of the pharmaceutical compositions for treating skin lesion according to the present invention, comprising a cerium salt on a collagen matrix and a dermatologically acceptable carrier. They were prepared to be used as an intermediate composition which is subsequently subjected to lyophilization by conventional techniques known in the art in order to form a dressing containing cerium nitrate in a concentration of 0.4% by weight (Formulations 7, 9 and 10) and 2.2% by weight (Formulations 8, 11 and 12) and bovine collagen type I.

The intermediate formulations 7-12 are examples of the pharmaceutical compositions according to the present invention, comprising a cerium salt on a collagen matrix and a dermatologically acceptable carrier. They contain cerium nitrate in a concentration of 0.014% by weight (Formulations 7, 9 and 10) and 0.075% by weight (Formulations 8, 11 and 12), bovine collagen type I in the gel form and water as the dermatologically acceptable carrier. Propylene glycol was used as emollient. Sodium alginate (Formulations 9 and 11) and calcium alginate (Formulations 10 and 12) were used as suspending agent and exudate absorber.

Formulation 7:

| Raw material | Preferred Concentration (% w/w) | Special Concentration (% w/w) | Properties |
|---|---|---|---|
| Bovine Collagen Type I (gel) | 1% to 95% | 75% | Hemostatic, chemotactic and matrix for cell migration |
| Cerium Nitrate | 0.001% to 5% | 0.014% | Antimicrobial agent, immunomodulator, anti-inflammatory (reduction of TNF-☐ levels). |
| Propylene Glycol | 1% to 20% | 10% | Emollient |
| Water | q.s.p. 100% | | Carrier |

Formulation 8:

| Raw material | Preferred Concentration (% w/w) | Special Concentration (% w/w) | Properties |
|---|---|---|---|
| Bovine Collagen Type I (gel) | 1% to 95% | 73% | Hemostatic, chemotactic and matrix for cell migration |
| Cerium Nitrate | 0.001% to 5% | 0.075% | Antimicrobian, immunomodulador, anti-inflammatory (reduction of TNF-☐ levels). |
| Propylene Glycol | 1% to 20% | 10% | Emollient |
| Water | | q.s.p. 100% | Carrier |

Formulation 9:

| Raw material | Preferred Concentration (% w/w) | Special Concentration (% w/w) | Properties |
|---|---|---|---|
| Bovine Collagen Type I (gel) | 1% to 95% | 75% | Hemostatic, chemotactic and matrix for cell migration |
| Cerium Nitrate | 0.001% to 5% | 0.014% | Antimicrobial agent, immunomodulator, anti-inflammatory (reduction of TNF-☐ levels). |
| Sodium alginate | 0.1% to 20% | 0.35% | Suspending agent, exudate absorber |
| Propylene Glycol | 1% to 20% | 10% | Emollient |
| Water | | q.s.p. 100% | Carrier |

Formulation 10:

| Raw material | Preferred Concentration (% w/w) | Special Concentration (% w/w) | Properties |
|---|---|---|---|
| Bovine Collagen Type I (gel) | 1% to 95% | 75% | Hemostatic, chemotactic and matrix for cell migration |
| Cerium Nitrate | 0.001% to 5% | 0.014% | Antimicrobial agent, immunomodulator, anti-inflammatory (reduction of TNF-☐ levels). |
| Calcium alginate | 0.1% to 20% | 0.35% | Suspending agent, exudate absorber |
| Propylene Glycol | 1% to 20% | 10% | Emollient |
| Water | | q.s.p. 100% | Carrier |

Formulation 11:

| Raw material | Preferred Concentration (% w/w) | Special concentration (% w/w) | Properties |
|---|---|---|---|
| Bovine collagen type I (gel) | 1% to 95% | 73% | Hemostatic, chemotactic and matrix for cell migration |
| Cerium Nitrate | 0.001% to 5% | 0.075% | Antimicrobial agent, immunomodulator, anti-inflammatory (reduction of TNF-☐ levels). |
| Sodium alginate | 0.1% to 20% | 0.35% | Suspending agent, exudate absorber |
| Propylene Glycol | 1% to 20% | 10% | Emollient |
| Water | | q.s.p. 100% | Carrier |

Formulation 12:

| Raw material | Preferred Concentration (% w/w) | Special concentration (% w/w) | Properties |
|---|---|---|---|
| Bovine collagen type I (gel) | 1% to 95% | 73% | Hemostatic, chemotactic and matrix for cell migration |
| Cerium Nitrate | 0.001% to 5% | 0.075% | Antimicrobial agent, immunomodulator, anti-inflammatory (reduction of TNF-☐ levels). |
| Calcium alginate | 0.1% to 20% | 0.35% | Suspending agent, exudate absorber |
| Propylene Glycol | 1% to 20% | 10% | Emollient |
| Water | | q.s.p. 100% | Carrier |

Thus, as mentioned above, the intermediate Formulations 7, 9 and 10 are lyophilized to form a dressing containing cerium nitrate in a concentration of 0.4% by weight and bovine collagen type I, and the intermediate Formulations 8, 11 and 12 are lyophilized to form a dressing containing cerium nitrate in a concentration of 2.2% by weight and bovine collagen type I.

After lyophilization, the dressing presents a spongy aspect, similar to a fiber frame. Then, the resulting dressing is sterilized through gamma radiation, ethylene oxide or electron beam sterilization systems.

All steps of the process for preparing the present invention conform to Manufacturing and Control Good Practice procedures as required by the national and international regulatory agencies.

The examples shown above are preferred and illustrative variations of the present invention and should not be interpreted as limitations to it. In this regard, it should be understood that the scope of the present invention comprehends the possibility of other variations to the composition, these being limited only by the context of the claims here incorporated, with possible equivalents hereon included.

Bacteriostatic Evaluation Test

Bacteriostatic evaluation of the present invention product was performed according to the "Manual de Saneantes do Instituto Nacional de Controle de Qualidade em Saúde—Item 8-B: Métodos para Avaliação da Atividade Inibitória de Preparações Líquida, Cremosa e Sólida—Método da Placa de Ágar"—January 1992, for the following microorganisms: *Staphylococcus aureus* ATCC 6538 and *Salmonella choler-*

*aesuis* ATCC 10708. Test result proved the bacteriostatic action of the product after a clear inhibition zone formed around the sample.

BIBLIOGRAPHIC REFERENCES

1—Sipos P, Gyõry H, Hagymási K, Ondrejka P, Blázovics A: Special wound healing methods used in ancient Egypt and the mythological background. World Journal of Surgery 2004, 28: 211-216.

2—Madelbaum S H, Di Santis E P, Madelbaum M H S: Cicatriza-ção: conceitos atuais e recursos auxiliares—parte I. Anais Bras Dermatologia 2003, 78(4): 393-408.

3—Odland G: The fine structure of the interrelationship of cells in the human epidermis. J Biophys Biochem Cytol 1958, 4:529.

4—Choucair M, Phillips T J. Wound Dressings. In: Freedberg, I M eds. Fitzpatrick's Dermatology in General Medicine. International Edition. McGraw Hill, 1999: 2954-1958.

5—Winter G D: Formation of a scab and the rate of epithelialization of superficial wounds in the skin of the young domestic pig. Nature 1962, 193:293.

6—Hinman CD et al: Effect of air exposure and occlusion on experimental human skin wounds. Nature 1963, 200:377.

7—Fitzpatrick Clark R A F: Mechanisms of Cutaneous Wound Repair; In: Freedberg, I M eds. Fitzpatrick's Dermatology in General Medicine. International Edition. McGraw Hill, 1999: 2954-1958.

8—Dadalti P e Neffá-Pinto J: Fisiologia da Reparação tecidual e suas implicações terapêuticas in: Azulay & Azulay: Dermatologia Quarta Edi-ção. Guanabara Koogan, Rio de Janeiro, RJ.

9—Hughes M A. The Science of wound healing. In: The Oxford European Wound Healing Course Handbook. Positif Press, 2002: 11-19.

10—Dadalti-Granja P: Úlceras de estase venosa: Fatores prog-nósticos e estudo piloto do use de epiderme cultivada em derme acelular. Tese de Doutorado. Rio de Janeiro, 2004.

11—Karukonda S R K, Flynn T C, Boh E E, McBurney E I, Russo G C, Millikan L E. The effects of drugs on wound healing: part I. Int Journal of Dermatol 2000, 39: 250-7.

12—Karukonda S R K, Flynn T C, Boh E E, McBurney E I, Russo G C, Millikan L E The effects of drugs on wound healing: part II. Int Journal of Dermatol 2000, 39: 321-333.

13—Hart J, Silcock D, Gunnigle S, Cullen B, Light N D, Watt P W: The role of oxidised regenerated cellulose/collagen in wound repair: effects in vitro on fibroblast biology and in vivo in a model of compromised healing. The Int Journal Of Bioch & Cell Biology 2002 (34): 1557-1570.

14—Mendez M V, Raffetto J D et al: The proliferative capacity of neonatal skin fibroblasts is reduced after exposure to venous ulcer fluid: a potential mechanism for senescence in venous ulcer. J Vasc Surgery 1999, 30, 4: 134-142.

15—Vu T H, Werb Z. Matrix Metalloproteinases: effectors of development and normal physiology. Genes & Development 2000, 14:2123-2133.

16—Steffensen B, Häkkinen L, Larjava H. Proteolytic events of wound-healing—Coordinated Interactions among matrix metalloproteinases (MMPs), Integrins and Extracellular Matrix Molecules. Crit Rev Oral Biol Med 2001, 12(5): 373-398.

17—Armstrong D G, Jude E B. The role of matrix metalloproteinases in wound healing. J Am Podiatr Med Assoc. 2002, 92(1):

18—Postlethwaite A E et al: Chemotactic attraction of human fibroblast to type I, II, and III collagens and collagen-derived peptides. Proc Natl Acad Sci USA 1978 75:871.

19—Damsky C H, Werb Z: Signal transduction by integrin receptors for extracellular matrix: Cooperative processing of extracellular information. Curr Opin Cell Biol 1992 4:772.

20—Xu J, Clark R A F: Extracellular matrix alters PDGF regulation of fibroblast integrins. J Cell Biol 1996, 132: 239.

21—Lin C Q, Bissell M J: Multi-faceted regulation of cell differentiation by extracellular matrix. FASEB J 1993, 7:737.

22—Wayner E A, Carter W G: Identification of multiple cell adhesion receptors for collagen and fibronectin in human fibrosarcoma cells possessing unique and common subunits. J Cell Biol 1989 105:1873.

23—Staatz W D et al: The membrane glycoprotein Ia-IIa (VLA-2) complex mediates the Mg 2 +-dependent adhesion of platelets to collagen. J Cell Biol 1989, 108:1917.

24—Ignatius M J et al: Molecular cloning of the rate integrin □1-subunit: A receptor for laminin and collagen. J Cell Biol 1990, 111:709.

25—Levenson S M et al: The healing of rat skin wounds. Ann Surg 1965, 161:293.

26—Monafo L. The use of Topical Cerium Nitrate-Silver Sulfadiazine in Major Burn Injuries. 1983; Panminerva Medica—v. 25: 151-154.

27—Burkes S & McCleskey C S. *The bacteriostatic activity of cerium, lanthanum, and thalium*. J Bacteriology 1947. 54: 417-425.

28—Monafo W W, Tandon S N, Ayvazian V H, Tuchshmidt J, Skinner A M, Deitz F. *Cerium Nitrate: A New Topical Antiseptic for Extensive Burns*. Surgery 1976; 80, p. 465-473.

29—Fox C L, Monafo W W, Ayvazian et al. *Topical chemotherapy for burns using cerium salts and silver sulfadiazine*. Surg. Gynecol. Obstet 1977; 144: 668.

30—Allgower M., Schoenenberger G. A., Sparkes B. G. Burning the largest immune organ. Burns, 1995, 21, 1: 7-47.

31—Deveci et al: Effects of Cerium Nitrate Bathing and Prompt Burn Wound Excision on Il-6 and TNF□ Levels in Burned Rats. Burns 2000, 26:41-5.

The invention claimed is:

1. A pharmaceutical composition for treating a skin lesion, formed by mixing a cerium salt with a collagen matrix gel and a dermatologically acceptable carrier and homogenizing to form a homogenous composition, wherein the collagen matrix gel is present in an amount of from 5% to 95% by weight.

2. The pharmaceutical composition according to claim 1, characterized in that the cerium salt is cerium nitrate.

3. The pharmaceutical composition according to claim 1, characterized in that the collagen used is bovine collagen type I.

4. The pharmaceutical composition according to claim 1, characterized in that the cerium salt is present in an amount of from 0.1% to 5% by weight, and the collagen matrix gel is present in an amount of from 1% to 95% by weight based on the total weight of the composition.

5. The pharmaceutical composition according to claim 4, characterized in that the cerium salt is present in an amount of 0.4% by weight and the collagen matrix gel is present in an amount of 75% by weight.

6. The pharmaceutical composition according to claim 4, characterized in that the cerium salt is present in an amount of 2.2% by weight and the collagen matrix gel is present in an amount of 73% by weight.

7. The pharmaceutical composition according to claim 1, characterized in that it further comprises a suspending agent.

8. The pharmaceutical composition according to claim 7, characterized in that the suspending agent is an alginate.

9. The pharmaceutical composition according to claim 7, characterized in that the suspending agent is present in an amount of from 0.1% to 20% by weight based on the total weight of the composition.

10. The pharmaceutical composition according to claim 1, characterized in that the dermatologically acceptable carrier is water.

11. The pharmaceutical composition according to claim 1, characterized in that it further comprises an emollient.

12. The pharmaceutical composition according to claim 11, characterized in that the emollient is propylene glycol.

13. The pharmaceutical composition according to claim 11, characterized in that the emollient is present in an amount of from 1% to 20% by weight based on the total weight of the composition.

14. The pharmaceutical composition according to claim 1, characterized in that it is designed for topical application in skin lesions involving the release, in human or animal organisms, of toxin related to microbial proteins or heat shock proteins (HSP); in burns involving the formation of burned skin toxin or lipoprotein complex (LPC); in chronic ulcerated skin lesions in which there is proteinase overproduction; and in skin lesions which were critically infected or colonized.

15. The pharmaceutical composition according to claim 7, characterized in that it is designed for topical application in skin lesions of difficult resolution, in which control of exudate overproduction is required.

16. The pharmaceutical composition according to claim 1, characterized in that it is designed for topical application in lesions selected from venous stasis ulcers, pressure ulcers, perforating plantar wounds and complex surgical wounds and burns.

17. A composition for preparing a dressing for treating a skin lesion formed by mixing a cerium salt with a collagen matrix gel and a dermatologically acceptable carrier and homogenizing to form a homogenous composition, wherein the collagen matrix gel is present in an amount of from 5% to 95% by weight.

18. The composition according to claim 17, characterized in that the cerium salt is cerium nitrate.

19. The composition according to claim 17, characterized in that the collagen used is bovine collagen type I.

20. The composition according to claim 17, characterized in that the cerium salt is present in an amount of from 0.001% to 5% by weight and the collagen matrix gel is present in an amount of from 5% to 95% by weight, based on the total weight of the composition.

21. The composition according to claim 20, characterized in that the cerium salt is present in an amount of 0.014% by weight and the collagen matrix gel is present in an amount of 75% by weight.

22. The composition according to claim 20, characterized in that the cerium salt is present in an amount of 0.075% by weight and the collagen matrix gel is present in an amount of 73% by weight.

23. The composition according to claim 17, characterized in that it further comprises a suspending agent.

24. The composition according to claim 23, characterized in that the suspending agent is an alginate.

25. The composition according to claim 23, characterized in that the suspending agent is present in an amount of from 0.1% to 20% by weight based on the total weight of the composition.

26. The composition according to claim 17, characterized in that the dermatologically acceptable carrier is water.

27. The composition according to claim 17, characterized in that it further comprises an emollient.

28. The composition according to claim 27, characterized in that the emollient is propylene glycol.

29. The composition according to claim 27, characterized in that the emollient is present in an amount of from 1% to 20% by weight-based on the total weight of the composition.

30. A dressing for treating skin lesion comprising a homogenized composition formed by mixing a cerium salt with a collagen matrix gel to form a homogenous dressing, wherein the collagen matrix gel is present in an amount of from 5% to 95% by weight.

31. The dressing according to claim 30, characterized in that the cerium salt is cerium nitrate.

32. The dressing according to claim 30, characterized in that the collagen used is bovine collagen type I.

33. The dressing according to claim 30, characterized in that the cerium salt is present in an amount of from 0.1% to 5% by weight based on the total weight of the dressing.

34. The dressing according to claim 33, characterized in that the cerium salt is present in an amount of 0.4% by weight.

35. The dressing according to claim 33, characterized in that the cerium salt is present in an amount of 2.2% by weight.

36. The dressing according to claim 30, characterized by being prepared by lyophilizing the composition comprising the cerium salt mixed with the collagen matrix gel and a dermatologically acceptable carrier.

37. The dressing according to claim 30, characterized by being sterilized through gamma radiation, ethylene oxide or electron beam sterilization systems.

38. A process for preparing a dressing for treating a skin lesion, characterized by comprising the steps of:
 a) providing a composition according to claim 17; and
 b) lyophilizing the composition of step a), thus forming a dressing for treating the skin lesion.

39. The process according to claim 38, characterized by further comprising the step of sterilizing the dressing formed in step b) through gamma radiation, ethylene oxide or electron beam sterilization systems.

40. A method for treating a skin lesion, characterized by applying the pharmaceutical composition according to claim 1 on said skin lesion.

* * * * *